United States Patent [19]

Miyazawa et al.

[11] Patent Number: 4,997,754

[45] Date of Patent: Mar. 5, 1991

[54] PROCESS FOR RECOVERING L-AMINO ACIDS FROM FERMENTATION LIQUORS CONTAINING THEM

[75] Inventors: Masashi Miyazawa, Yokohama; Toyokazu Kaneko, Sagamihara; Tetsuya Kaneko, Kawasak; Kenich Yarita, Yokohama, all of Japan; Shigenori Mori, Raleigh, N.C.; Kinzo Iitani, Raleigh, N.C.; Masaki Yamamoto, Raleigh, N.C.

[73] Assignee: Ajinomoto Co., Inc., Tokyo, Japan

[21] Appl. No.: 83,590

[22] Filed: Aug. 10, 1987

[51] Int. Cl.$^5$ .............................................. C12P 13/04
[52] U.S. Cl. .................................. 435/106; 435/107; 435/108; 435/110; 435/114; 435/115; 435/116
[58] Field of Search ................................ 435/106–108, 435/110, 114, 115, 116

[56] References Cited

U.S. PATENT DOCUMENTS

| | | | |
|---|---|---|---|
| 4,523,999 | 6/1985 | Toyoshi et al. | 210/639 |
| 4,663,048 | 5/1987 | Tanaka et al. | 210/639 |
| 4,734,401 | 3/1988 | Blouin | 426/443 |

Primary Examiner—Robert J. Warden
Assistant Examiner—Timothy M. McMahon
Attorney, Agent, or Firm—Oblon, Spivak, McClelland, Maier & Neustadt

[57] ABSTRACT

A process for recovering a high-purity L-amino acid from a fermentation liquor obtained by fermentation or an enzymic method, which comprises removing the impurities contained in said fermentation liquor by passing said fermentation liquor through an ultrafilter membrane and then through an ion-exchange or adsorbent resin; concentrating or cooling the effluent thus obtained to result in crystallization of said L-amino acid, and isolation said crystalline L-amino acid from said fermentation liquor.

10 Claims, 6 Drawing Sheets

PROCESS FOR RECOVERING L-AMINO ACIDS FROM FERMENTATION LIQUORS CONTAINING THEM

BACKGROUND OF THE INVENTION

Field of the Invention

L-amino acid fermentation liquors contain large quantities of microbial cells and soluble proteins, which must be removed because they retard the growth of amino acid crystals and otherwise negatively affect efficient recovery of the amino acid product.

A great variety of other impurities (inorganic salts, sugar, pigments, etc.) derived from the culture medium used and from the metabolism of the microorganisms employed are also contained in the fermentation liquor, and these must also be removed by sophisticated combinations of various isolation and purification techniques, such as ion exchange, activated charcoal treatment, and crystallization.

In the past, isolation of amino acids from fermentation liquors containing them and purification thereof, have been performed as follows: microbial cells and other insoluble impurities are first removed by centrifugal separation, filtration, coagulation or sedimentation, the pH of the resulting solution is adjusted so that the amino acid being purified will be in cationic form, and the cationic amino acid thus formed is adsorbed onto a strongly acidic cation-exchange resin. The adsorbed amino acid is eluted with a dilute alkali solution, the eluate is decolorized with activated charcoal, and the free amino acid or salt thereof is separated in crystalline form by concentration, cooling or neutralization. The crystals thus obtained may be further purified, as required, through recrystallization. A large number of amino acids are produced based on this process on an industrial scale, including arginine, glutamine, histidine, isoleucine, lysine, proline, threonine, serine and valine.

In industrial operations, centrifugal settlers, nozzle-discharge type, continuous centrifugal separators and basket-type centrifugal separators are frequently used for removal of microbial cells and other insoluble impurities, while vacuum and press filters using a precoat of diatomaceous earth are principally employed for filtration.

However, it is difficult to completely remove microbial cells by centrifugal force, and filtration is unable to remove soluble proteins. This gives rise to various problems in the succeeding steps: clogging of columns packed with ion-exchange resin, retarded growth of amino acid crystals, coagulation of denatured proteins during heating and concentration, which contaminate the crystals of amino acid and significantly lower its purity, and others. The result is that ion-exchange resin treatment is not as effective as it could be, and recrystallization has to be conducted repeatedly to obtain crystals with the desired purity.

On the other hand, anionic substances, pigments and polymers contained as impurities are also responsible for retardation of crystal growth, as well as lowered purity and discoloration of separated crystals. Use of anion-exchange resin, amphoteric ion-exchange resin or adsorbent synthetic resin have been adopted to remove such impurities. In this case, too, the above-mentioned soluble proteins tend to be adsorbed on these resins, thus markedly diminishing their actions and often making their regeneration impossible as a result of irreversible adsorption.

In view of the above drawbacks of the prior art methods, there remains a need for new and improved methods for recovering high purity amino acids from fermentation liquors.

SUMMARY OF THE INVENTION

Accordingly, it is an object of the present invention to develop a technique capable of removing both microbial cells and polymeric impurities from fermentation liquors used to produce amino acids.

It is yet another object of the present invention to develop a technique to remove substances that are responsible for retardation of crystal growth and low purity of separated amino acid crystals.

It is yet another object of the present invention to establish a simple process for recovering high purity crystals of L-amino acids which eliminates the need for ion exchange.

According to the present invention, high purity crystals of an amino acid can be recovered from fermentation liquors by a simple process if the impurities contained therein are removed by passing the fermentation liquor through an ultrafiltration membrane and then through an ion-exchange or adsorbent resin, followed by concentration or cooling of the effluent thus obtained.

DETAILED DESCRIPTION OF THE PREFERRED EMBODIMENTS

Figure 1:
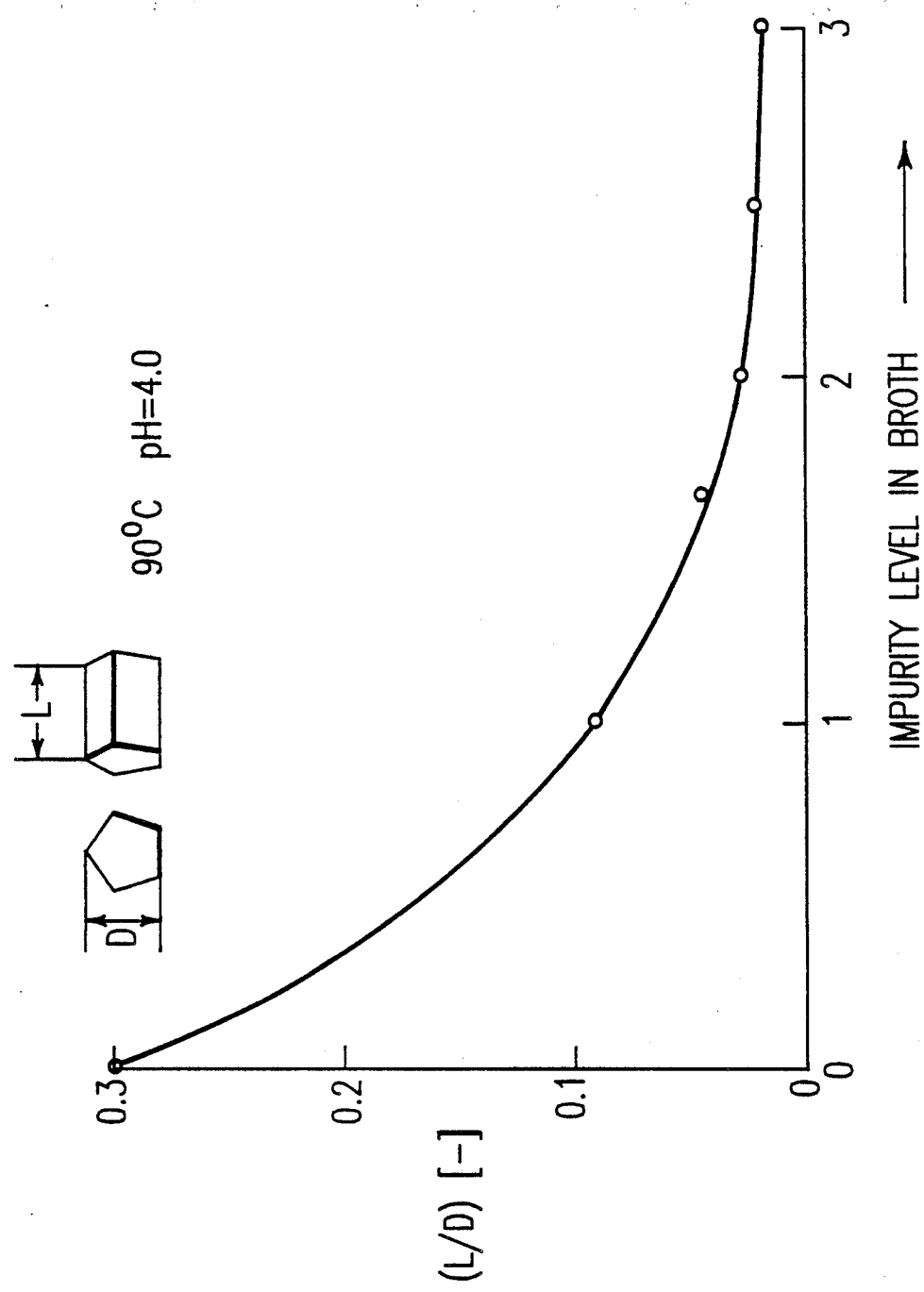
FIG. 1 shows the effect on crystal growth of lysine by broth impurities.
Figure 2:
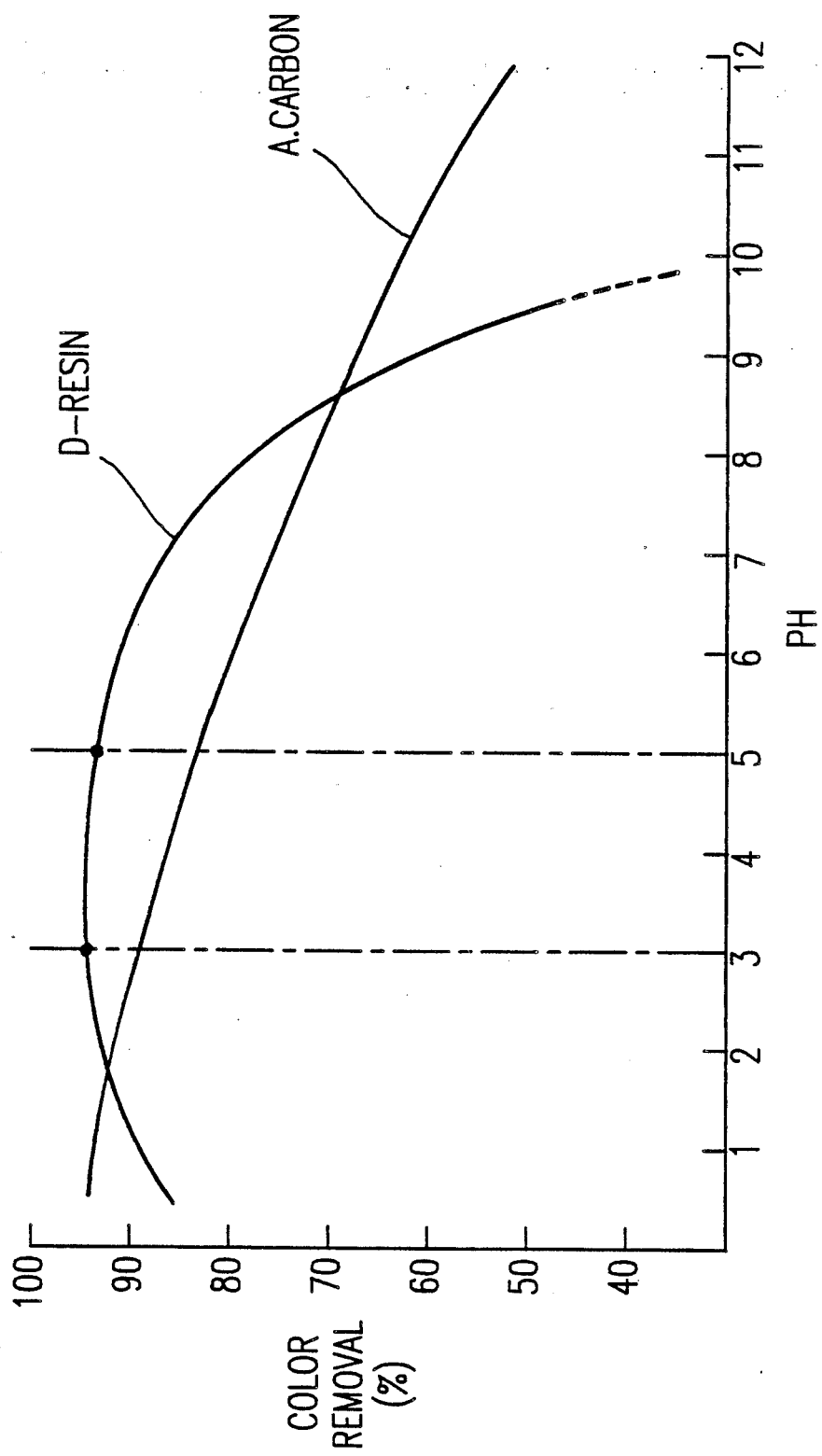
FIG. 2 shows the decolorization ability of D-resin and activated carbon as a function of pH.
Figure 3:
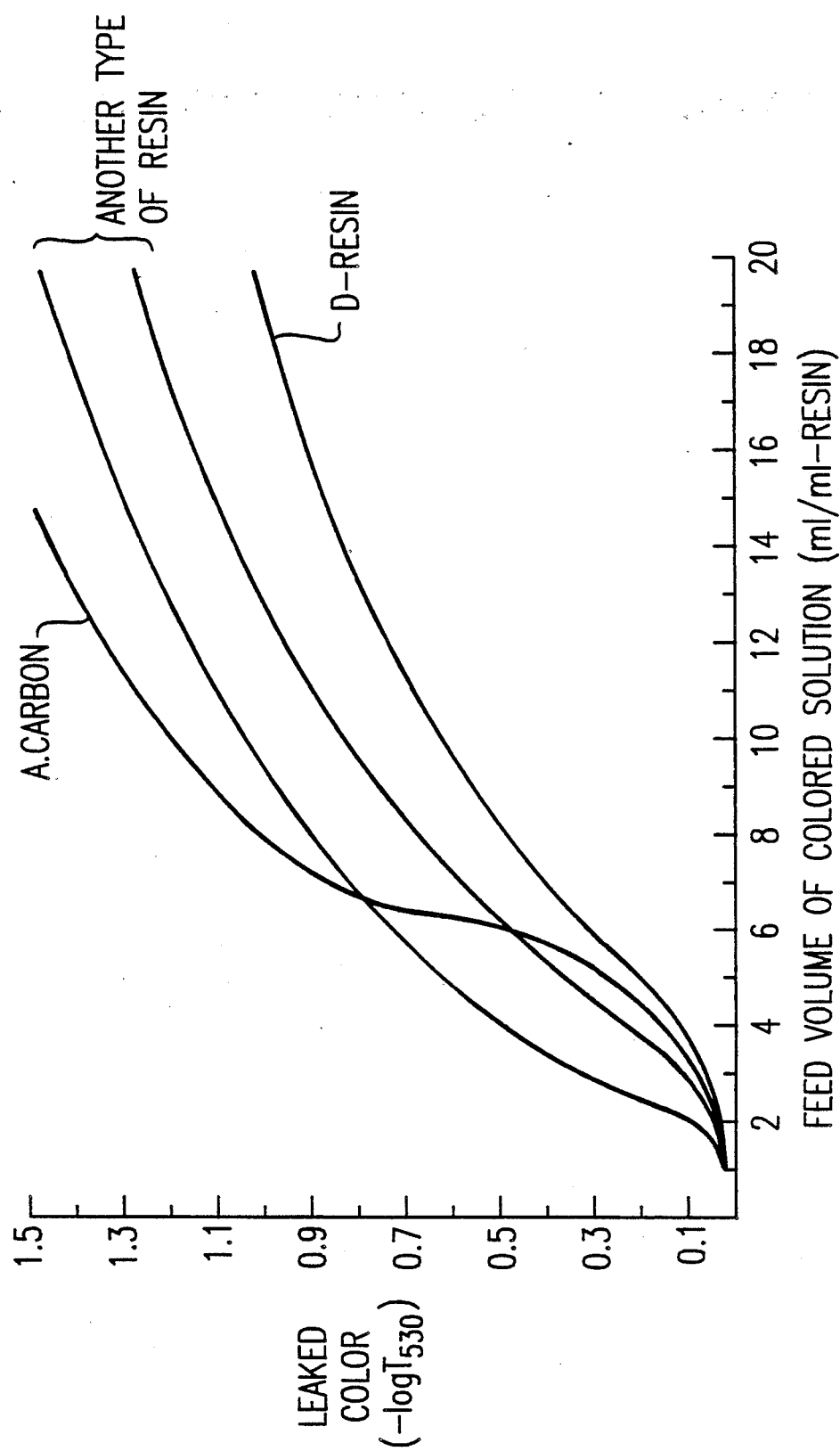
FIG. 3 shows the decolorization curves for activated carbon, D-resin, and others as a function of the feed volume of colored solution.
Figure 4:
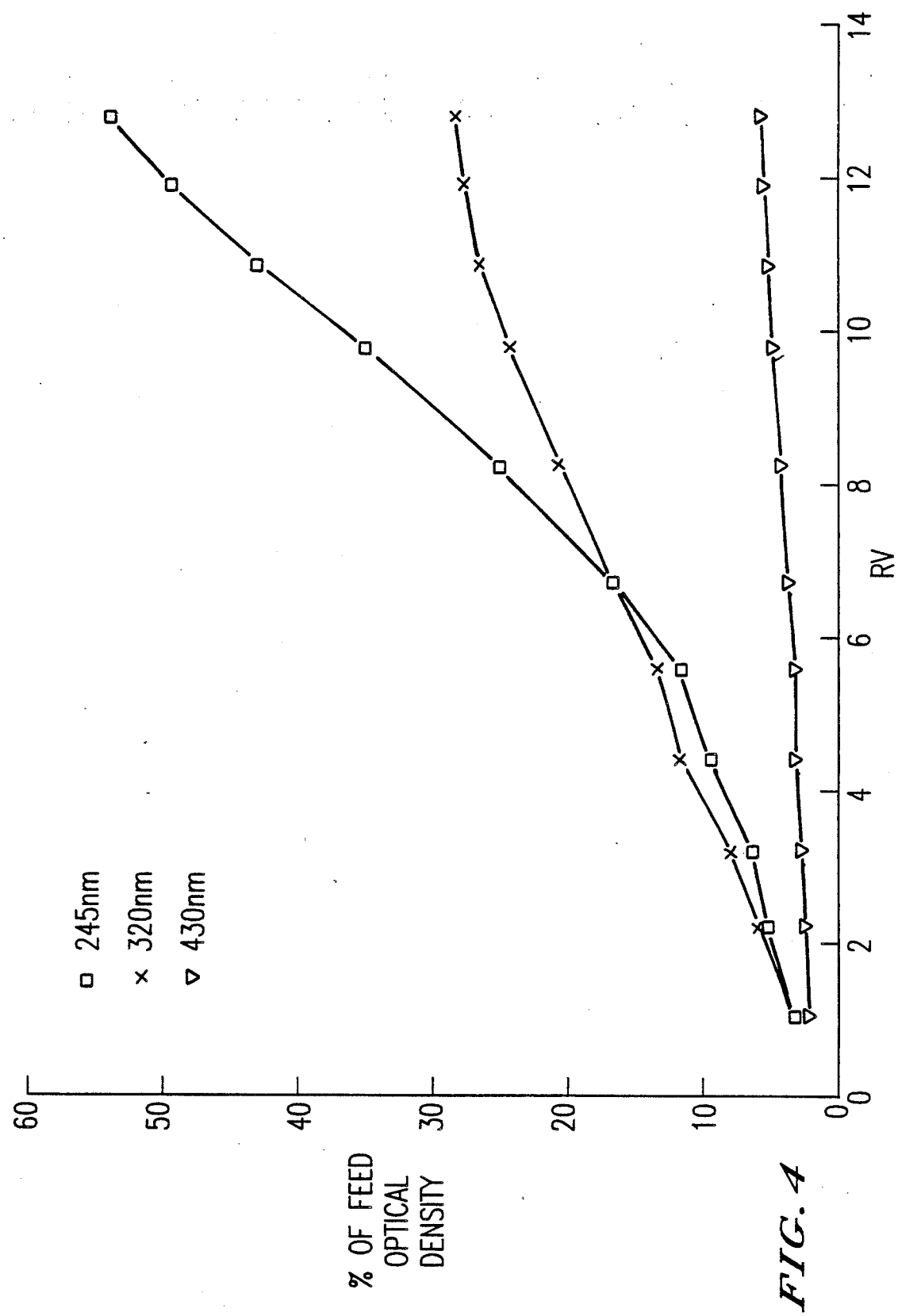
FIGS. 4 and 5 show decolorization curves for D-resin.
Figure 5:
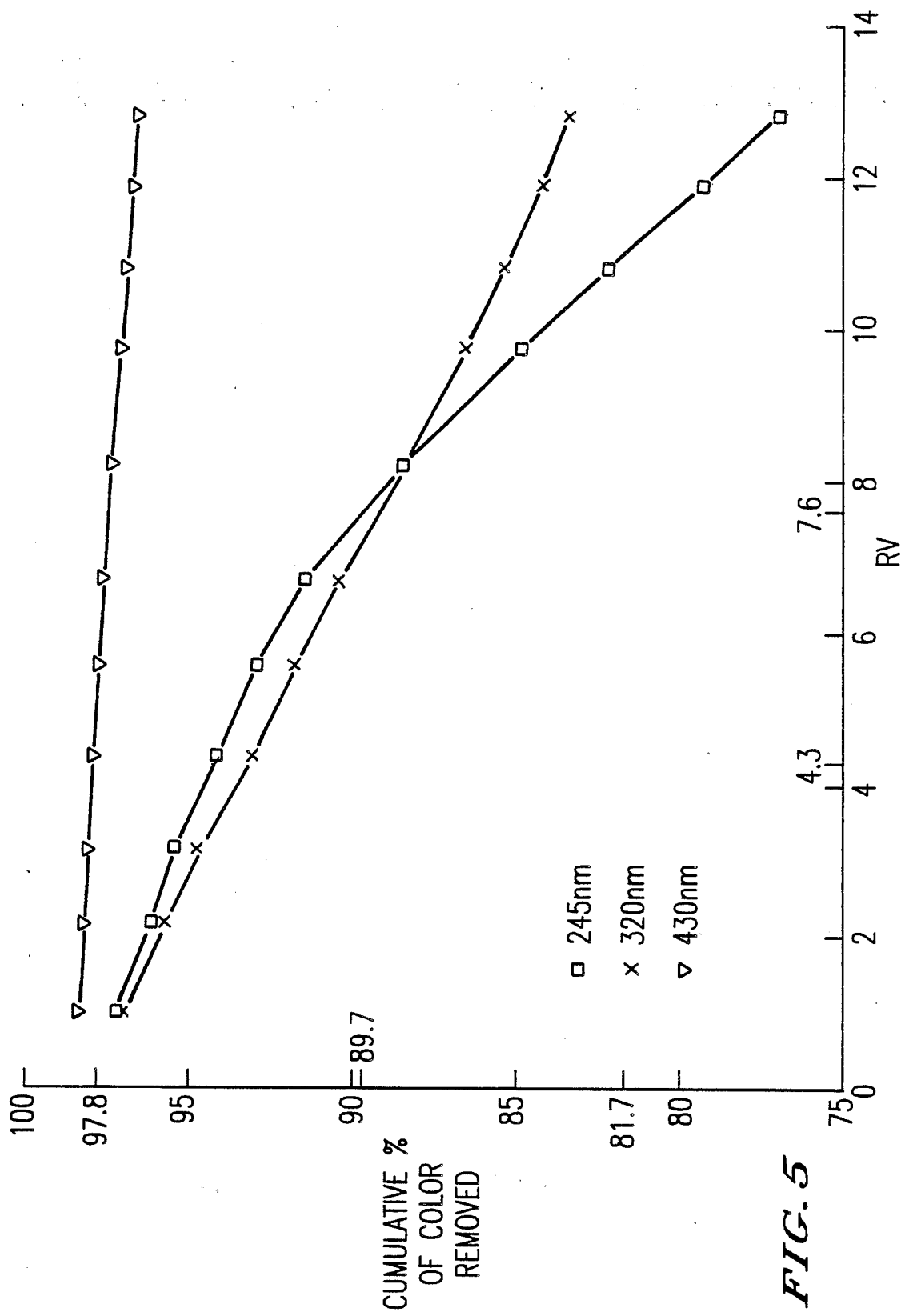
Figure 6:
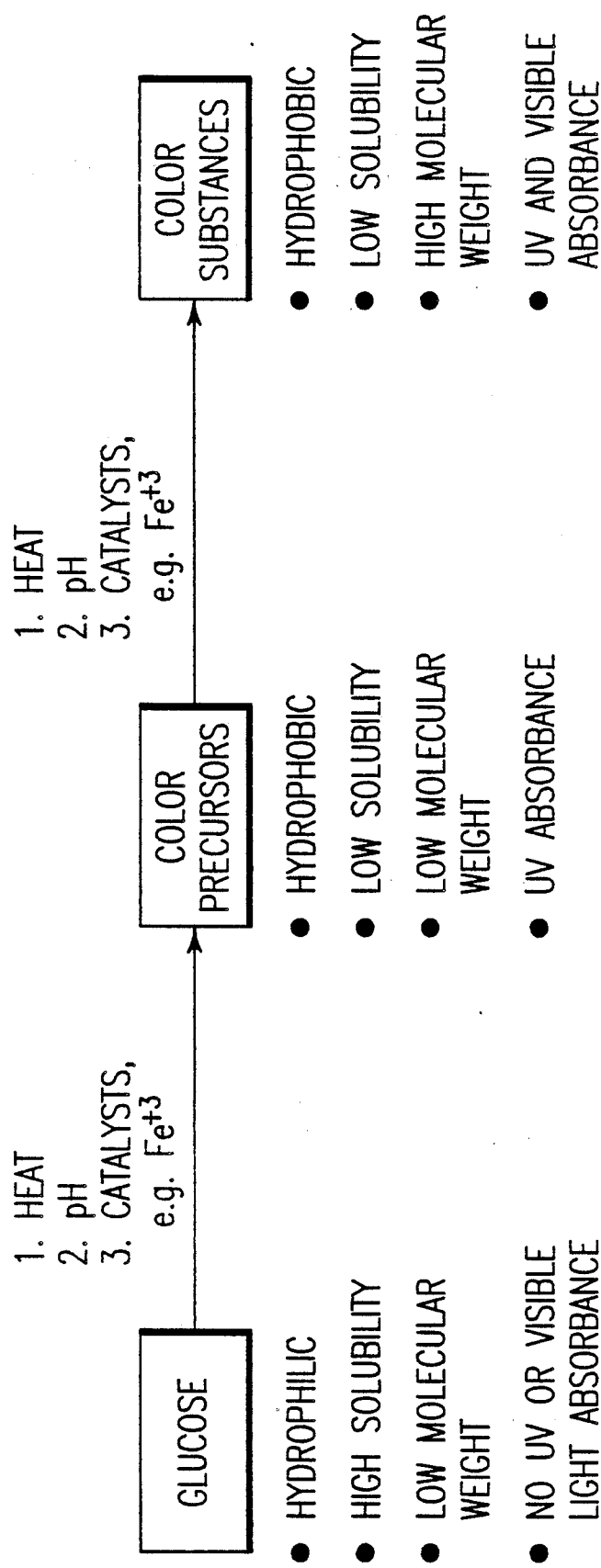
FIG. 6 shows a diagram on color formation in fermentation broths.

The cell size of typical microorganisms is generally considered to be 1.5 to 1.1 $\mu$m for the genus Escherichia, 1.0 to 0.5 $\mu$m for the genus Staphylococcus, and 1.0 to 0.22 $\mu$m for the genus Pseudomonas (the smallest of all). On the contrary, the exclusion size of precoat filters is said to be 1.0 $\mu$m. With proteins, the molecular size of albumin with a molecular weight of 67,000 is about 30 Å ($=0.003$ $\mu$m) and that of cytochrome C with a molecular weight of 13,000 is about 20 Å ($=0.002$ $\mu$m). It is apparent that these impurities cannot be completely removed by centrifugal sedimentation or precoat filtration on an industrial basis.

Ultrafiltration, a technique recently applied to water treatment and cheese whey purification, is based in principle on diffusion, unlike ordinary filtration, and is therefore applicable to fractionation in the molecular weight range of from 300,000 to 1,000 by the use of ultrafilter membranes with different pore sizes. This technique is also extensively used in the biochemical field for purification of proteins and other purposes; many reports have disclosed its use for the industrial manufacture of high-purity proteins and removal of endotoxins.

The present inventors attempted to apply ultrafiltration to the removal of microbial cells and soluble proteins contained in fermentation liquor. It was demonstrated that the wet-cell volume can be concentrated to 70 to 80% and that up to 99.5% of soluble, low-molecular substances like amino acids can be recovered if the concentrate obtained above is diluted with water and again subjected to ultrafiltration. The filtrate resulting from filtration through an ultrafilter membrane is transparent, with removal of some pigments and lowering of viscosity being observed.

A problem associated with ordinary filtration is a gradual decrease in filtration speed due to clogging of the filter used. In ultrafiltration, on the other hand, the membrane shows less tendency to be clogged because of its specific working mechanism (permeation by diffusion) and fouling substances built up on the membrane surface can be effectively eliminated by maintaining a certain fluid flow (agitation of the solution being treated or high-speed circulation), thus ensuring a stable permeation speed. Membranes may be cleaned with common cleaners suited to the membrane material, such as dilute alkalis, dilute solutions of sodium hypochlorite, commercial cleaners and specific cleaning agents supplied from the membrane manufacturers. A recovery rate of 95 to 98% (evaluated by permeation speed of pure water) can thus be obtained.

Ultrafilter membranes may be used in any known form (e.g., plain film, hollow fiber, tubular and spiral) and may be made of any material. Preferred materials are polysulfone, polyvinylidene fluoride, polyacrylonitrile and cellulose. Most preferred are polysulfone or cellulose, flat or hollow fiber type ultrafiltration membranes.

The pH and temperature of the fermentation liquor being treated is somewhat limited by the equipment materials and ultrafilter membrane used; membranes made of polysulfone, however, can be used over wide temperature and pH ranges (from 15° to 80° C. and from pH 1 to 14), offering practically no problem. A preferred pH range is from 2.5 to 8.0. A preferred temperature range is 20° to 70° C.

The pressure employed during ultrafiltration membrane operation is preferably 4.0–6.0 bars (inlet) and 1.0–2.0 bars (outlet). The molecular weight range for fractionation is preferably 6000–50,000. More preferably, the range is 6000–10,000. The flux is preferably 70 $1/m^2/h$-150 $1/m^2/h$.

Optimum concentrations of the amino acids in the fermentation broth are as follows:

| | | |
|---|---|---|
| L-Ile | 20–40 g/l | |
| L-Trp | 20–21 g/l | |
| L-Ala | 95–130 g/l | |
| L-Val | 40–70 g/l | |
| L-Thr | 40–90 g/l | |
| L-His | 15–40 g/l | |
| L-Phe | 20–30 g/l | |

The filtrate passing through an ultrafilter membrane is then freed from remaining impurities in the next step, followed by crystallization. In conventional processes, a cation-exchange resin is generally used for removal of the impurities; the pH of the filtrate is adjusted so that the amino acid being purified will be converted into a cationic form. The cationic amino acid thus formed is adsorbed on a strongly acidic cation-exchange resin to remove the impurities as effluent, and the adsorbed amino acid is recovered by elution with an alkali solution.

This method is an excellent technique utilizing the basicity of the amino group contained in amino acids, but is unsatisfactory in selectivity because all the substances that can be converted into cations are adsorbed on the resin together with the amino acid being isolated. In addition, the cation-exchange resin commonly used for this purpose has a stryrene-divinylbenzene copolymer backbone structure, and hence tends to adsorb hydrophobic substances, such as pigments and proteins, because the part of the resin molecule other than the cation-exchange groups (sulfonic acid groups) is highly hydrophobic. Upon contact with an eluent (an alkali), these adsorbed cationic and hydrophobic substances are eluted for the most part due to changes in electric charge and ionic strength. Thus the effect of eliminating impurities is rather low, in view of the intricate operations (adsorption and elution) which are performed, the large quantities of acids and alkalis which are consumed and the huge volume of waste water which is discharged.

The advantage of the amino acid fermentation process over the protein decomposition method is that only one type of amino acid can be accumulated at high concentrations in the fermentation liquor by the culture of a specific microorganism. The progress of strain breeding techniques has been striking in recent years, with the result that formation of by-products has been markedly decreased. With the enzymic method, in particular, no by-product is formed at all in some cases. Thus, the conventional cation-exchange process is rapidly losing its significance in chemical, energy-saving and environmental aspects.

In view of the above, an emerging problem is that high-purity crystals of an amino acid cannot be obtained by concentrating or cooling its fermentation liquor just freed from microbial cells. Tryptophan fermentation liquor, for example, contains large quantities of hydrophobic substances and pigments formed by oxidative decomposition and polymerization of the indole ring, which not only affect the growth of crystals, resulting fine crystals, but also are incorporated into the separated crystals and cannot be effectively removed by recrystallization. In alanine fermentation liquor, aspartic acid remaining as an impurity affects the growth of crystals to produce fine crystals and is incorporated in the separated crystals of alanine. The same is true of isoleucine and valine fermentation liquor, which becomes turbid during concentration; the impurities formed are incorporated in the separated crystals, thus greatly lowering their purity.

The inventors have discovered that two groups of substances are responsible for such contamination of amino acid crystals. One group includes polymeric substances having a molecular weight of 10,000 or higher, such as soluble proteins, nucleic acids and polysaccharides. It was demonstrated that these polymeric substances are readily insolublized through denaturation and coagulation as a result of heating and changes in pH and ionic strength, thus depositing on the surface or otherwise contaminating the crystals of amino acid and significantly lower their purity. These impurities include 2-acetyl-pyrrole, 2,5-dimethyl tetrahydrofuran, 2-hydroxymethylimidazole, 2-n-butyl tetrahydrofuran, furfural alcohol, indole, butyrolactam, trimethyl hydrazine, acetic acid, acetone, butylamine, and propionic acid. Most of these impurities are color precursors which have UV absorption in the wavelength range of 280–340 mμ.

The other group includes pigments and hydrophobic substances with lower molecular weights, which, during crystallization of an amino acid, are adsorbed on its growing surfaces to retard the crystal growth, thereby producing fine, flat and coalesced crystals. The resulting crystals contain an enormous volume of mother liquor, making solvent washing ineffective and thus lowering the purity of the final products. The substances of this group are contained in the fermentation liquor in minute amounts but have a critical effect upon crystal growth.

The process of this invention addresses the removal of both types of impurities. As stated above, substances of the first group (polymeric substances) can be easily removed by the use of ultrafiltration. Substances of the second group (crystal-growth inhibiting substance) are contained in minute amounts and cannot be eliminated by the cation-exchange method. It was then attempted to remove these impurities by selective adsorption on a certain functional resin, and to obtain high-purity amino acid crystals from the resulting effluent through a single crystallization step.

The crystal-growth inhibiting substances are highly hydrophobic in nature and hence might be removed by passing the liquor containing the same through a suitable adsorbent resin. Weakly basic anion-exchange resins and amphoteric ion-exchange resins are generally known as adsorbent resins for decolorizing. The inventors have found that these resins exhibit, in addition to decolorizing action, outstanding effects when used for pretreatment of fermentation liquor under discussion. Decolorization activity in the present fermentation liquors is excellent with the resins employed herein.

The weakly basic anion-exchange resins may be any of four known types: polystyrene, polyphenolic, epoxy or polyacrylate. Of these, the polystyrene and polyacrylate types are preferred. These resins generally have attached thereto primary, secondary or tertiary amino groups, —$NH_2$, —NHR, or —$NR_2$, where R can be any alkyl group (preferably $C_{1-10}$), including substituted alkyl groups (preferably $C_{6-12}$). These are exemplified by the Amberlite ® IRA series (Rohm & Haas), Duolite A300 series (Duolite) and DIAION WA series (Mitsubishi Chemical Industries). Two especially preferred weak base resins are Ionac ® A-365 (acrylate type) and Amberlite IRA. Ionac ® A-365, manufactured by Sybron, a division of Ionac, is a weakly basic polyacrylate based anion exchange resin with a porous gelular bead structure. Amberlite ® IRA-68 is a weakly basic, gelular, acrylic, anion exchange resin containing only tertiary amine groups.

The amphoteric ion-exchange resins are porous aromatic polymers having amino and phenolic hydroxyl groups on the surface and are exemplified by HS and KS resins (Hokuetsu Carbon Industries).

D-resin is a preferred amphoteric ion-exchange resin which contains both amine and phenol groups on the surface of a porous type phenolic resin. This resin cannot split salts of strong acids or bases. However, D-resin can adsorb substances which are weak acids or bases. D-resin operates in acidic or neutral pH conditions for adsorption. Elution of adsorbed substances occurs in alkaline solution.

The preferred pH range for the resin treatment step is from 2.5–8.0. The preferred temperature range is 20°–70° C. The preferred feed rate is 3–5, more preferably 4, resin vol(l)/hr. The preferred feed volumes are as follows:

|       | D-resin          | Anion resin      |
|-------|------------------|------------------|
| L-Ile | 700–750 g/l-resin | 130–140 g/l-resin |
| L-Trp | 450–550 g/l-resin | —                |
| L-Ala | —                | 550–650 g/l-resin |
| L-Val | 1100–1300 g/l-resin | 200 g-300 g/l-resin |
| L-Thr | 900–1100 g/l-resin | —                |
| L-His | 900–1000 g/l-resin | —                |
| L-Phe | 600–700 g/l-resin | —                |

If an untreated fermentation liquor is directly treated with these resins, proteins, pigments, nucleic acids and oils irreversibly deposit or become adsorbed to cover the active surface, thus significantly diminishing their activity. In addition, these fouling substances, when an acid, alkali or alcohol is used as regenerating agent, coagulate as a result of denaturation and clog the resin, often making its regeneration impossible.

The inventors passed an amino acid fermentation liquor through an ultrafilter membrane and then treated the resulting effluent with these resins, and found that decolorization or removal of hydrophobic substances can be accomplished very effectively. Comparison of the properties of the fermentation liquor before and after treatment with the resin revealed a sharp drop in UV absorption at about 280 to 350 nm (near ultraviolet region) and removal of substances having molecular weights of about 1,000 to 3,000 in gel chromatography. Hydrophobic chromatography (methanol gradient technique) also showed elimination of highly hydrophobic substances eluted at methanol concentrations from about 30 to 50% as well as a marked decrease of fluorescent substances, indicating effective elimination of hydrophobic substances containing benzene or purine rings. As an accompanying effect, efferverscence during concentration was markedly diminished, making the concentration operation far easier. Thus the inventors succeeded in accomplishing high-purity crystallization of amino acids by a simple process including, as pretreatment steps, ultrafiltration and treatment with an adsorbent resin.

The invention now being generally described, the same will be better understood by reference to certain specific examples which are included herein for purposes of illustration only and are intended to be limiting of the invention or any embodiment thereof, unless specified.

EXAMPLES

Example 1

The fermentation liquor containing L-alanine (L-Ala) used in this example was obtained from an enzymic reaction in a reactor tank with an agitator using L-aspartic acid (L-Asp) as substrate. This reaction is catalyzed by Pseudomonas strain No. 618 (ATCC 19121) having high L-aspartate β-carboxylase activity (EC 4.1.1.12).

The fermentation liquor was diluted with tap water to an L-Ala concentration of 99 g/1 (unreacted L-Asp: 0.13 g/1), adjusted to pH 3.3 with 95% sulfuric acid, and forced to pass through a regenerated-cellulose ultrafilter membrane (nominal fractionating molecular weight: 10,000) to remove suspended solids, oil and polymeric substances.

The clear solution thus obtained was passed through a column packed with OH-form Amberlite IRA-68 (a weakly basic anion-exchange resin) to eliminate remaining L-Asp, other anions and pigments. The total load of L-Ala was 600 g/1 resin.

The effluent from the column was neutralized to pH 6.0 with 35% hydrochloric acid and concentrated under reduced pressure to an L-Ala concentration of 110 g/1. The resulting solution was further concentrated in a calandria evaporator with an agitator at 75° C. under reduced pressure to a final L-Ala concentration of 620 g/1. The concentrated slurry thus obtained was transferred to a jacketed crystallizer with an agitator, where it was cooled down to 10° C. to complete crystallization. The slurry was charged into a basket-type centrifugal separator and separated into crystals and mother liquor. The cake of crystals was subjected to centrifugal washing in the basket using tap water (11.8 liters for 100 Kg of L-Ala). The purity of L-Ala crystals thus obtained was 99% or higher (content of L-Asp: 0.01% of less) and the transmittance of an aqueous solution of the crystals was 97%.

The mother liquor separated above, which contained 135 g/1 of L-Ala, was concentrated in a calandria evaporator with an agitator at 75° C. under reduced pressure to an L-Ala concentration of 136 g/1, the resulting slurry was cooled to 10° C. in a jacketed crystallizer with an agitator, the second crystals thus formed were separated from the mother liquor in a basket-type centrifugal separator, and the cake of crystals was subjected to centrifugal washing using tap water (26.1 liters for 100 Kg L-Ala).

The overall yield of L-Ala (sum of the first and second crystals) was 94.3% based on the amount contained in the original broth.

Comparative Example 1a

Using the same enzymatic reaction liquor of L-Ala described Example 1, the clear permeate was adjusted to pH 6.0; then directly concentrated without resin treatment, and the first crystals were obtained in the same way as in Example 1. The purity of crystals was 98.7% containing 0.08% of L-Asp, and light transmittance was 91.9%. The overall yield of L-Ala, including first and second crystals, was 91.9%; and both crystals were fine compared with Example 1. This result was probably caused by retardation of crystal growth derived from L-Asp.

Example 2

A fermentation liquor containing 21 g/1 of L-isoleucine (L-Ile) was adjusted to pH 3.0 with 35% hydrochloric acid, and forced to pass through an ultrafilter membrane (nominal fractionating molecular weight: 6,000) to remove microbial cells and polymeric substances.

The clear solution thus obtained was passed through a column packed with Agent D to eliminate pigments and fluorescent substances. The total load of L-Ile was 720 g/1 resin.

The decolorized effluent from the column was concentrated in a rotary evaporator at 50° C. under reduced pressure to a final L-Ile concentration of 200 g/1. The concentrated slurry was neutralized to pH 5.6 with 27% caustic soda solution and transferred to a crystallizer with an agitator, where crystallization was performed by cooling from 50° to 20° C. under programmed control. The slurry thus obtained was charged into a basket-type centrifugal separator and separated into crystals and mother liquor. The cake of crystals was subjected to centrifugal washing in the basket using tap water (60 ml for 300 g of L-Ile). The purity of L-Ile crystals thus obtained was 95% and the transmittance of an aqueous solution of the crystals was 94%.

The mother liquor separated above, which contained 34 g/1 of L-Ile, was concentrated under reduced pressure to an L-Ile concentration of 100 g/1, the resulting slurry was cooled to 10° C. in a crystallizer with an agitator, the second crystals thus formed were separated from the mother liquor in a basket-type centrifugal washing using tap water (10 ml liters for 30 g L-Ile).

The overall yield of L-Ile (sum of the first and second crystals) was 94.3% based on the amount contained in the original broth.

When the original fermentation liquor was pretreated by ultrafiltration alone (with the treatment with Agent D omitted), the purity of final crystals was 92%, the yield was 89% and transmittance of an aqueous solution was 34%.

When the original fermentation liquor was freed from microbial cells by centrifugal separation, followed by treatment with Agent D, the purity of final crystals was 87%, the yield was 90% and transmittance of an aqueous solution was 72%.

Comparative Example 2a

Using the same fermentation liquor of L-Ile described in Example 2, the clear permeate was passed through a packed column with strongly acidic cation-exchange resin (Na type) to absorb L-Ile as a cation, then L-Ile was eluted with 0.5N-sodium hydroxide solution. The eluate from the column was concentrated and crystallized by the same method as in Example 2. The purity of the crystals thus obtained was 92% L-Ile; and the light transmittance was 49%.

Comparative Example 2b

Using the same fermentation liquor of L-Ile described Example 2, the clear permeate was adjusted to pH 5.5 with 27% sodium hydroxide solution, then directly concentrated and crystallized using the same method as in Example 2, without resin treatment. The purity of the crystals thus obtained was 87% L-Ile; and the light transmittance was 12%. These crystals were so fine they could hardly be separated.

Comparative Example 2c

Using the same fermentation liquor of L-Ile described Example 2, after pH adjustment, the microbial cells were separated by a continuous centrifugal separator, and supernatent that was not clear was obtained. When this liquor was passed through a column packed with HS resin as in Example 2, the sediment was clogged in an upper layer of the resin, so the flow rate gradually decreased. Thus, it was necessary to employ back washing. The effluent from the column was concentrated and crystallized using the same method as described in Example 2. The purity of the crystals thus obtained was 82% L-Ile; and the light transmittance was 67%.

Example 3

A fermentation liquor containing 50 g/1 of L-threonine (L-Thr) was adjusted to pH 3.0 with 35% hydrochloric acid, and forced to pass through an ultrafilter membrane (nominal fractionating molecular weight:

6,000) to remove microbial cells and polymeric substances.

The clear solution thus obtained was passed through a column packed with Agent D to eliminate pigments and fluorescent substances. The total load of L-Thr was 1,000 g/l·resin.

The decolorized effluent from the column was neutralized with 27% caustic solution to pH 5.6 then concentrated in a rotary evaporator at 50° C. under reduced pressure to an L-Thr concentration of 120 g/l. Seed crystals (10%) are added and concentration was further continued to a final level of 350 g/l. The concentrated slurry was transferred to a crystallizer with an agitator, where crystallization was performed by cooling from 50° to 20° C. under programmed control. The slurry thus obtained was charged into a basket-type centrifugal separator and separated into crystals and mother liquor. The cake of crystals was subjected to centrifugal washing in the basket using tap water (150 ml for 300 g of L-Thr). The purity of L-Thr crystals thus obtained was 97% or higher (content of homoserine: 2%) and the yield was 83% based on the amount contained in the original broth.

Example 4

A fermentation liquor containing 65 g/l of L-valine (L-Val) was adjusted to pH 3.0 with 35% hydrochloric acid, and forced to pass through an ultrafilter membrane (nominal fractionating molecular weight: 6,000) to remove microbial cells and polymeric substances.

The clear solution thus obtained was passed through a column packed with Agent D to eliminate pigments and fluorescent substances. The total load of L-Val was 1,200 g/l·resin.

The decolorized effluent from the column was concentrated in a rotary evaporator at 50° C. under reduced pressure to a final L-Val concentration of 200 g/l. The concentrated slurry was neutralized with 27% caustic soda solution to pH 5.6 and transferred to a crystallizer with an agitator, where crystallization was performed by cooling from 50° to 10° C. under programmed control. The slurry thus obtained was charged into a basket-type centrifugal separator and separated into crystals and mother liquor. The cake of crystals was subjected to centrifugal washing in the basket using tap water (50 ml for 240 g of L-Val). The purity of L-Val crystals thus obtained was 96% or higher.

The mother liquor separated above, which contained 50 g/l of L-Val, was concentrated at 50° C. under reduced pressure to an L-Val concentration of 106 g/l. The slurry thus obtained was separated into crystals and mother liquor in a basket-type centrifugal separator, and the cake of second crystals thus obtained was subjected to centrifugal washing using tap water (10 ml for 30 g of L-Val).

The overall yield of L-Val (sum of the first and second crystals) was 91.3% based on the amount contained in the original broth.

Example 5

A fermentation liquor containing 23 g/l of L-histidine (L-His) was adjusted to pH 3.0 with 35% hydrochloric acid, and forced to pass through an ultrafilter membrane (nominal fractionating molecular weight: 6,000) to remove microbial cells and polymeric substances.

The clear solution thus obtained was passed through a column packed with Agent D to eliminate pigments and fluorescent substances. The total load of L-His was 900 g/l resin.

The decolorized effluent from the column was concentrated in a rotary evaporator at 50° C. under reduced pressure to a final L-His concentration of 250 g/l. The concentrated slurry was transferred to a crystallizer with an agitator, where crystallization was performed by cooling from 50° to 10° C. under programmed control. The slurry thus obtained was charged into a basket-type centrifugal separator and separated into crystals of L-His·HCl·$H_2O$ and mother liquor. The cake of crystals was subjected to centrifugal washing in the basket using tap water (80 ml for 400 g of L-His·HCl·$H_2O$). The purity of the crystals thus obtained was 99% or higher and the yield was 82% based on the amount contained in the original broth.

Example 6

A fermentation liquor containing 20 g/l of L-tryptophan (L-Trp) was adjusted to pH 4.0 with 60% sulfuric acid, and forced to pass through an ultrafilter membrane (polysulfone; fractionating molecular weight: 6,000) to remove microbial cells and polymeric substances.

The clear solution thus obtained was passed through a column packed with Agent D (an amphoteric ion-exchange resin prepared by condensation between m-phenylenediamine and resorcinol) to eliminate pigments derived from L-Trp. Part of the L-Trp was adsorbed on Agent D in this operation, which was subsequently recovered by passing deionized water through the column. The total load of L-Trp was 500 g/l·resin.

The aqueous solution used to recover the adsorbed L-Trp was combined with the major effluent, and the combined solution was neutralized with 5% caustic soda solution to pH 4.0 and concentrated in a calandria evaporator with an agitator at 45° C. under reduced pressure to an L-Trp concentration of 150 g/l. The concentrated slurry was transferred to a jacketed crystallizer with an agitator, where crystallization was completed by cooling from 45° to 5° C.

The cooled slurry thus obtained was charged into a basket-type centrifugal separator and separated into crystals and mother liquor. The cake of crystals was subjected to centrifugal washing in the basket using deionized water (90 liters for 100 Kg of L-Trp). The collected crystals were slurried with deionized water (400 liters for 100 Kg of crystals) in a jacketed crystallizer with an agitator, the slurry was stirred at 20° C. for one hour sand then separated into crystals and mother liquor in a basket-type centrifugal separator. The cake of crystals was again subjected to centrifugal washing in the basket using deionized water (90 liters for 100 Kg of L-Trp) and then dried in a tray dryer at 40° C. under reduced pressure. The yield was 72% and the purity of the crystals was 99.9% (content of other amino acids: less than 0.01%). The transmittance of a solution of 1 g of the crystals in 100 ml deionized water was 93%.

Comparative Example 6a

A fermentation liquor containing 20 g/l of L-tryptophan (L-Trp) was adjusted to pH 4.0 with 60% sulfuric acid, and forced to pass through an ultrafilter membrane (polysulfone; fractionating molecular weight: 6,000) to remove microbial cells and polymeric substances.

The clear solution thus obtained was concentrated in a calandria evaporator with an agitator at 45° C. under reduced pressure to an L-Trp concentration of 100 g/l and the concentrated slurry was transferred to a jacketed crystallizer with an agitator, where crystallization was completed by cooling from 45° to 5° C.

The slurry thus obtained was separated into crystals and mother liquor in a basket-type centrifugal separator, and the cake of crystals was subjected to centrifugal washing in the basket using deionized water (90 liters for 100 Kg of L-Trp). The collected crystals were slurried with deionized water (400 liters for 100 Kg of crystals) in a jacketed crystallizer with an agitator, the slurry was stirred at 20° C. for one hour and then separated into crystals and mother liquor in a basket-type centrifugal separator. The cake of crystals wa again subjected to centrifugal washing in the basket using deionized water (90 liters for 100 Kg of L-Trp) and then dried in a tray dryer at 40° C. under reduced pressure. The yield was 66% and the purity of the crystals was 98.2% (contents of other amino acids: less than 0.1%). The transmittance of a solution of 1 g of the crystals in 100 ml deionized water was 9.2%.

Purification was further continued as follows. The crystals obtained above were again slurried with deionized water (1,000 liters for 100 Kg of L-Trp), the slurry was heated to 35° C. and brought into solution by adjusting the pH to 2.0 with 60% sulfuric acid. Activated charcoal (20 Kg for 100 Kg of L-Trp) was added to the solution, and the mixture was stirred for one hour and filtered. The filtrate was held at 35° C. and neutralized to pH 6.0 by slowly adding 10% caustic soda solution to effect crystallization, and the resulting slurry was cooled down to 5° C.

The cooled slurry thus obtained was charged into a basket-type centrifugal separator and separated into crystals and mother liquor. The cake of crystals was subjected to centrifugal washing in the basket using deionized water (90 liters for 100 Kg of L-Trp). The collected crystals were slurried with deionized water (400 liters for 100 Kg of crystals) in a jacketed crystallizer with an agitator, the slurry was stirred at 20° C. for one hour and then separated into crystals and mother liquor in a basket-type centrifugal separator. The cake of crystals was again subjected to centrifugal washing in the basket using deionized water (90 liters for 100 Kg of L-Trp) and then dried in a tray dryer at 40° C. under reduced pressure. The yield was 76% and the purity of the crystals was 99.1% (contents of other amino acids: less than 0.05%). The transmittance of a solution of 1 g of the crystals in 100 ml deionized water was 20.5%.

Comparative Example 6b

A fermentation liquor containing 20 g/l of L-tryptophan (L-Trp) was adjusted to pH 4.0 with 60% sulfuric acid, and treated in a centrifugal settler to remove microbial cells.

The supernatant was passed through a column packed with a cation-exchange resin (degree of cross-linking: 4%; Na salt form) to a total L-Trp load of 150 g/l·resin to adsorb L-Trp. The adsorbed L-Trp was eluted by introducing an eluent, maintained at pH 12.5 to 13.0 with 27% caustic soda solution, into the column at its bottom while properly fluidizing the resin and returning the effluent from the top of the column back to the eluent tank. This operation was continued for two hours, and the column was then treated with 0.5% caustic soda solution. The eluate containing high-concentration L-Trp obtained above was transferred to a jacketed crystallizer with an agitator, where it was heated to 45° C. and neutralized with 60% sulfuric acid to effect crystallization, followed by cooling to complete crystallization.

The cooled slurry thus obtained was charged into a basket-type centrifugal separator and separated into crystals and mother liquor. The cake of crystals was subjected t centrifugal washing in the basket using deionized water (90 liters for 100 Kg of L-Trp). The collected crystals were slurried with deionized water (400 liters for 100 Kg of crystals) in a jacketed crystallizer with an agitator, the slurry was stirred at 20° C. for one hour and then separated into crystals and mother liquor in a basket-type centrifugal separator. The cake of crystals was again subjected to centrifugal washing in the basket using deionized water (90 liters for 100 Kg of L-Trp) and then dried in a tray dryer at 40° C. under reduced pressure. The yield was 62% and the purity of the crystals was 99.0% (contents of other amino acids: less than 0.05%). The transmittance of a solution of 1 g of the crystals in 100 ml deionized water was 15%. No appreciable enhancement of transmittance was achieved after the product was further purified by usual methods.

Table 1 lists the transmittance and other data for the crystals obtained in EXAMPLES 6-1, -2 and -3. The effect achieved by combination of ultrafiltration (UF) treatment with Agent D is evident from the table.

TABLE 1

| EXAMPLE | 6 | 6-A | 6-B |
|---|---|---|---|
| Flow | UF + Agent D | UF | Centrifuging + CER |
| Transmittance | 93.0% | 9.2% | 15.0% |
| Yield (Recrystallized Product) | 72% | 66% | 62% |
| Transmittance | — | 20.5% | — |
| Yield | — | 76% | — |

Example 7

A fermentation liquor containing 55 g/l of L-valine (L-Val) was forced to pass through a regenerated-cellulose ultrafilter membrane (nominal fractionating molecular weight: 10,000) to remove microbial cells and polymeric substances. The volume of the broth was 3.84 l, and it contained a total of 211 g of L-Val.

The clear solution thus obtained, which had a pH of 7.5, was passed through a column packed with Ionac A-365 weakly basic ion exchange resin, to remove anionic impurities. The packed volume of the resin was 1.0 l, and the resin was in the free base form. The total load of L-Val was 205 g/l-resin. The effluent from the column had a pH of 8.2.

The effluent from the column was concentrated in a rotary evaporator at 50° C. under reduced pressure, to remove ammonia. The final L-Val concentration was 75 g/l.

The pH of the concentrated solution was adjusted to 1.0, using 35% hydrochloric acid. The liquor at pH 1.0 was then concentrated further in a rotary evaporator at 70° C. under reduced pressure to a final L-Val concentration of 300 g/l. After concentration, the solution had a volume of 680 ml, and contained 204 g of L-Val.

The concentrated solution was transferred to a crystallizer vessel with an agitator, and then 204 ml of 35% hydrochloric acid was added slowly, to effect crystallization of L-Val·HCl·$H_2O$. After addition of hydrochloric acid was completed, crystallization was continued by cooling from 70° C. to 10° C. at a controlled rate.

The slurry thus obtained was charged into a basket-type centrifugal separator, and separated into crystals and mother liquor. The cake of crystals was subjected to centrifugal washing in the basket, using 51 ml of an aqueous solution of 20% hydrochloric acid (31.5 ml per 100 g of L-Val).

The yield of L-Val·HCl·H$_2$O crystals was 288.8 g wet weight (179.3 g as L-Val free base). The overall yield was 85% based on the amount in the original broth.

Example 8

A fermentation liquor containing 24 g/l of L-isoleucine (L-Ile) was forced to pass through a regenerated-cellulose ultrafilter membrane (nominal fractionating molecular weight: 10,000) to remove microbial cells and polymeric substances. The volume of the broth was 3.55 l, and it contained a total of 85 g of L-Ile.

The clear solution thus obtained, which had a pH of 7.4, was passed through a column packed with Ionac A-365 weakly basic ion exchange resin, to remove anionic impurities. The packed volume of the resin was 1.0 l, and the resin was in the free base form. The total load of L-Ile was 139 g/l-resin. The effluent from the column had a pH of 8.2.

The effluent from the column was concentrated in a rotary evaporator at 50° C. under reduced pressure, to remove ammonia. The final L-Ile concentration was 40 g/l.

The pH of the concentrated solution was adjusted to 1.0, using 35% hydrochloric acid. The liquor at pH 1.0 was then concentrated further in a rotary evaporator at 70° C. under reduced pressure to a final L-Ile concentration of 240 g/l. The solution after concentration had a volume of 340 ml, and contained 82 g of L-Val.

The concentrated solution was transferred to a crystallizer vessel with an agitator, and then 120 ml of 35% hydrochloric acid was added slowly, to effect crystallization of L-Ile·HCl·H$_2$O. After addition of the hydrochloric acid was completed, crystallization was continued by cooling from 70° C. to 10° C. at a controlled rate.

The slurry thus obtained was charged into a basket-type centrifugal separator, and separated into crystals and mother liquor. The cake of crystals was subjected to centrifugal washing in the basket, using 30 ml of an aqueous solution of 20% hydrochloric acid (42 ml per 100 g of L-Ile).

The yield of L-Ile·HCl·H$_2$O crystals was 134.7 g wet weight (71.4 g as L-Ile free base). The overall yield was 84% based on the amount in the original broth.

Many modifications and variations of the present invention are possible in light of the above teachings. Therefore, it is to be understood that within the scope of the appended claims, the invention may be practiced otherwise then as specifically described.

I claim:

1. A process for recovering a high-purity L-amino acid from a fermentation liquor obtained by fermentation or an enzymic method, which comprises removing the impurities contained in aid fermentation liquor by passing said fermentation liquor through an ultrafilter membrane and then through an adsorbent resin selected from the group consisting of weakly basic anion-exchange resins and amphoteric ion-exchange resins; concentrating or cooling the effluent thus obtained to result in crystallization of said L-amino acid, and isolating said crystalline L-amino acid from said fermentation liquor.

2. The process according to claim 1 wherein said ultrafilter membrane has a form selected from the group consisting of plain film, hollow fiber, tubular and spiral.

3. The process of claim 1, wherein said ultrafilter membrane is made of a material selected from the group consisting of polysulfone, polyvinylidene fluoride, polyacrylonitrile, and cellulose.

4. The process of claim 1, wherein said ultrafilter membrane is made of regenerated cellulose or polysulfone.

5. The process of claim 1, wherein said ultrafilter membrane has a nominal fractionating molecular weight of from 6000 to 50,000.

6. The process of claim 1, wherein said weakly basic ion-exchange resin is made of polystyrene or polyacrylonitrile, each of which carries primary, secondary or tertiary amino groups.

7. The process of claim 1, wherein the ultrafiltration step is carried out at a pH from 2.5 to 8.0, at a temperature of from 20° to 70° C., with an inlet pressure of 4.0–6.0 bars and an outlet pressure of 1.0–2.0 bars, and a flux of 70 l/m$^2$/h–150 l/m$^2$/h.

8. The process of claim 1, wherein the amino acid and concentration thereof for ultrafiltration are selected from the following group:

| | |
|---|---|
| L-Ile | 20–40 g/l |
| L-Trp | 20–21 g/l |
| L-Ala | 95–130 g/l |
| L-Val | 40–70 g/l |
| L-Thr | 40–90 g/l |
| L-His | 15–40 g/l |
| L-Phe | 20–30 g/l |

9. The process of claim 1, wherein said adsorbent resin step is carried out at a pH of from 2.5–8.0, at a temperature of from 20°–70° C., and a feed rate of from 3–5 resin vol(l)/hr.

10. The process of claim 1, wherein said adsorbent resin is a D-resin or anion resin, and wherein the feed volume of the amino acid for the adsorbent resin step is selected from the group consisting of:

| | D-resin | Anion resin |
|---|---|---|
| L-Ile | 700–750 g/l-resin | 130–140 g/l-resin |
| L-Trp | 450–550 g/l-resin | — |
| L-Ala | — | 550–650 g/l-resin |
| L-Val | 1100–1300 g/l-resin | 200 g–300 g/l-resin |
| L-Thr | 900–1100 g/l-resin | — |
| L-His | 900–1000 g/l-resin | — |
| L-Phe | 600–700 g/l-resin | — |

* * * * *